(12) United States Patent
Adachi et al.

(10) Patent No.: US 6,323,017 B1
(45) Date of Patent: Nov. 27, 2001

(54) PLATELET ACTIVATING FACTOR ACETYLHYDROLASE, AND GENE THEREOF

(75) Inventors: Hideki Adachi; Masafumi Tsujimoto, both of Asaka; Hiroyuki Arai; Keizo Inoue, both of Tokyo, all of (JP)

(73) Assignee: Suntory Limited, Osaka (JP)

( * ) Notice: Subject to any disclaimer, the term of this patent is extended or adjusted under 35 U.S.C. 154(b) by 0 days.

(21) Appl. No.: 09/196,222

(22) Filed: Nov. 20, 1998

Related U.S. Application Data

(62) Division of application No. 08/886,152, filed on Jun. 30, 1997, now Pat. No. 5,880,273.

(30) Foreign Application Priority Data

Jun. 28, 1996 (JP) .................................................. 8-188369

(51) Int. Cl.⁷ .............................. C12N 9/14; C12N 9/00; C12N 9/20
(52) U.S. Cl. .......................... 435/195; 435/183; 435/198
(58) Field of Search ..................................... 435/183, 195, 435/198

(56) References Cited

FOREIGN PATENT DOCUMENTS

| 0638646A2 | 2/1995 | (EP) . |
| 95/09921 | * 4/1995 | (WO) . |
| WO 97/12984 | 4/1997 | (WO) . |

OTHER PUBLICATIONS

K. Hattori, et al., The Journal of Biological Chemistry, vol. 270, No. 38, pp. 22308–22313, "Purification and Characterization Of Platelet–Activating Factor Acetylhydrolase II From Bovine Liver Cytosol", Sep. 22, 1995.

D.M. Stafforini, et al., The Journal of Biological Chemistry, vol. 268, No. 6, pp. 3857–3865, "The Platelet–Activating Factor Acetylhydrolase From Human Erythrocytes. Purification and Properties", Feb. 25, 1993.

K. Hattori, et al., The Journal of Biological Chemistry, vol. 271, No. 51, pp. 33032–33038, "cDNA Cloning And Expression OF Intracellular Platelet–Activating Factor (PAF) Acetylhydrolase II", Dec. 20, 1996.

Adachi et al, "cDNA cloning of human cytosolic platelet–activating factor acetylhydrolase γ–subunit and its mRNA expression in human tissues", Biochemical and Biophysical Research Communication, vol. 214, No. 180–187, Sep. 5, 1995.

Hattori et al, "The catalytic subunit of bovine brain platelet–activating factor acetylhydrolose is a novel type of serine esterase", The Journal of Biological Chemistry, vol. 269, No. 37. pp. 23150–23155, Sep. 16, 1994.

Hattori et al, "Purification and Characterization of bovine brain platelet–activating factor acetylhydrolase", The Journal of Biological Chemistry, vol. 268, No. 25, pp. 18748–18753, Sep. 5, 1993.

* cited by examiner

Primary Examiner—Ponnathapu Achutamurthy
Assistant Examiner—Peter P. Tung
(74) Attorney, Agent, or Firm—Oblon, Spivak, McClelland, Maier & Neustadt, P.C.

(57) ABSTRACT

The present invention relates to an isolated human protein having platelet activating factor acetylhydrolase activity.

3 Claims, No Drawings

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
       (A) LENGTH: 392 amino acids
       (B) TYPE: amino acid
       (C) STRANDEDNESS: single
       (D) TOPOLOGY: linear (ii) MOLECULE TYPE: peptide (vi) ORIGINAL SOURCE:
       (A) ORGANISM: BOVINE (Bos taurus)

(xi) SEQUENCE DESCRIPTION: SEQ ID NO:1:

```
Met Gly Val Asn Gln Ser Val Ser Phe Pro Pro Val Thr Gly Pro His
 1               5                  10                  15

Leu Val Gly Cys Gly Asp Val Met Glu Gly Gln Ser Leu Gln Gly Ser
                20                  25                  30

Phe Phe Arg Leu Phe Tyr Pro Cys Gln Glu Ala Glu Glu Thr Ser Glu
            35                  40                  45

Gln Pro Leu Trp Ile Pro Arg Tyr Glu Tyr Cys Ala Gly Leu Ala Glu
        50                  55                  60

Tyr Leu Lys Phe Asn Lys Arg Trp Gly Gly Leu Leu Phe Asn Leu Gly
65                  70                  75                  80

Val Gly Ser Cys Arg Leu Pro Val Ser Trp Asn Gly Pro Phe Lys Thr
                85                  90                  95

Lys Asp Ser Gly Tyr Pro Leu Ile Ile Phe Ser His Gly Met Gly Ala
                100                 105                 110

Phe Arg Thr Val Tyr Ser Ala Phe Cys Met Glu Leu Ala Ser Arg Gly
            115                 120                 125

Phe Val Val Ala Val Pro Glu His Arg Asp Gly Ser Ala Ala Ala Thr
        130                 135                 140

Cys Phe Cys Lys Gln Thr Pro Glu Glu Asn Gln Pro Asp Asn Glu Ala
145                 150                 155                 160

Leu Lys Glu Glu Trp Ile Pro His Arg Gln Ile Glu Glu Gly Glu Lys
                165                 170                 175

Glu Phe Tyr Val Arg Asn Tyr Gln Val His Gln Arg Val Ser Glu Cys
            180                 185                 190

Val Arg Val Leu Lys Ile Leu Gln Glu Val Thr Ala Gly Gln Ala Val
        195                 200                 205

Leu Asn Ile Leu Pro Gly Gly Leu Asp Leu Met Thr Leu Lys Gly Gly
    210                 215                 220

Ile Asp Val Ser Arg Val Ala Val Met Gly His Ser Phe Gly Gly Ala
225                 230                 235                 240

Thr Ala Ile Leu Ala Leu Ala Lys Glu Met Gln Phe Arg Cys Ala Val
                245                 250                 255

Ala Leu Asp Ala Trp Met Phe Pro Leu Glu His Asp Phe Tyr Pro Thr
            260                 265                 270

Ala Arg Gly Pro Ile Phe Phe Ile Asn Ala Glu Lys Phe Gln Thr Val
        275                 280                 285

Glu Thr Val Asn Leu Met Lys Lys Ile Cys Asp Gln His His Gln Ser
    290                 295                 300
```

```
Arg Ile Ile Thr Val Leu Gly Ser Val His Arg Ser Leu Thr Asp Phe
305                 310                 315                 320

Val Phe Val Ala Gly Asn Trp Ile Ser Lys Phe Phe Ser Ser His Thr
            325                 330                 335

Arg Gly Ser Leu Asp Pro Tyr Glu Gly Gln Glu Thr Val Val Arg Ala
            340                 345                 350

Met Leu Ala Phe Leu Gln Lys His Leu Asp Leu Lys Glu Asp Tyr Asp
            355                 360                 365

Gln Trp Asn Asn Phe Ile Glu Gly Ile Gly Pro Ser Leu Thr Pro Gly
    370                 375                 380

Ala Pro His His Leu Ser Ser Leu
385                 390
```

(2) INFORMATION FOR SEQ ID NO:2:

(i) SEQUENCE CHARACTERISTICS:
        (A) LENGTH: 1665 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: BOVINE (Bos taurus)

(ix) FEATURE:
        (A) NAME/KEY: CDS
        (B) LOCATION: 111..1286

(xi) SEQUENCE DESCRIPTION: SEQ ID NO:2:

```
GTCGACCCAC GCGTCCGAGT TGACCGTCTG GGCTGTTTCT GAGGGTCAAC GTGACTCGCC          60

GTCAAGTTCA GCCACTGCCC AAGTCGTCGT TCAGTTCAGT TGGTTATGAG ATG GGG           116
                                                          Met Gly
                                                           1

GTC AAC CAG TCT GTG AGC TTC CCA CCC GTC ACG GGA CCC CAC CTC GTA          164
Val Asn Gln Ser Val Ser Phe Pro Pro Val Thr Gly Pro His Leu Val
      5                   10                  15

GGC TGT GGG GAT GTG ATG GAG GGT CAG AGC CTC CAG GGC AGC TTC TTT          212
Gly Cys Gly Asp Val Met Glu Gly Gln Ser Leu Gln Gly Ser Phe Phe
 20                  25                  30

CGA CTG TTC TAC CCG TGC CAA GAG GCA GAG GAG ACC TCG GAG CAG CCC          260
Arg Leu Phe Tyr Pro Cys Gln Glu Ala Glu Glu Thr Ser Glu Gln Pro
 35                  40                  45                  50

CTG TGG ATT CCC CGC TAT GAG TAC TGC GCT GGC CTG GCC GAA TAC CTA          308
Leu Trp Ile Pro Arg Tyr Glu Tyr Cys Ala Gly Leu Ala Glu Tyr Leu
             55                  60                  65

AAG TTT AAT AAG CGC TGG GGG GGG TTA CTG TTC AAC CTG GGT GTG GGA          356
Lys Phe Asn Lys Arg Trp Gly Gly Leu Leu Phe Asn Leu Gly Val Gly
         70                  75                  80

TCT TGT CGC CTG CCT GTT AGC TGG AAT GGC CCC TTT AAA ACA AAG GAC          404
Ser Cys Arg Leu Pro Val Ser Trp Asn Gly Pro Phe Lys Thr Lys Asp
         85                  90                  95

TCT GGA TAC CCC TTG ATC ATC TTC TCT CAT GGC ATG GGA GCC TTC AGG          452
Ser Gly Tyr Pro Leu Ile Ile Phe Ser His Gly Met Gly Ala Phe Arg
        100                 105                 110

ACA GTG TAT TCA GCC TTC TGC ATG GAG CTG GCT TCT CGT GGC TTT GTG          500
Thr Val Tyr Ser Ala Phe Cys Met Glu Leu Ala Ser Arg Gly Phe Val
115                 120                 125                 130

GTT GCT GTA CCA GAG CAC AGG GAT GGG TCA GCT GCG GCC ACC TGT TTC          548
Val Ala Val Pro Glu His Arg Asp Gly Ser Ala Ala Ala Thr Cys Phe
```

|  |  |  |  |  | 135 |  |  |  | 140 |  |  |  |  | 145 |  |  |
|---|---|---|---|---|---|---|---|---|---|---|---|---|---|---|---|---|
| TGC | AAG | CAG | ACC | CCA | GAG | GAG | AAC | CAG | CCT | GAC | AAT | GAG | GCC | CTG | AAG | 596 |
| Cys | Lys | Gln | Thr | Pro | Glu | Glu | Asn | Gln | Pro | Asp | Asn | Glu | Ala | Leu | Lys |  |
|  |  |  | 150 |  |  |  |  | 155 |  |  |  |  | 160 |  |  |  |
| GAG | GAA | TGG | ATC | CCC | CAC | CGT | CAA | ATT | GAG | GAA | GGG | GAG | AAG | GAA | TTC | 644 |
| Glu | Glu | Trp | Ile | Pro | His | Arg | Gln | Ile | Glu | Glu | Gly | Glu | Lys | Glu | Phe |  |
|  |  | 165 |  |  |  |  | 170 |  |  |  |  | 175 |  |  |  |  |
| TAT | GTT | CGG | AAC | TAC | CAG | GTG | CAT | CAG | AGG | GTG | AGC | GAG | TGT | GTG | AGG | 692 |
| Tyr | Val | Arg | Asn | Tyr | Gln | Val | His | Gln | Arg | Val | Ser | Glu | Cys | Val | Arg |  |
|  | 180 |  |  |  |  | 185 |  |  |  |  | 190 |  |  |  |  |  |
| GTG | TTG | AAG | ATC | CTA | CAA | GAG | GTC | ACT | GCT | GGG | CAG | GCC | GTT | CTC | AAC | 740 |
| Val | Leu | Lys | Ile | Leu | Gln | Glu | Val | Thr | Ala | Gly | Gln | Ala | Val | Leu | Asn |  |
| 195 |  |  |  |  | 200 |  |  |  |  | 205 |  |  |  |  | 210 |  |
| ATC | TTG | CCT | GGC | GGA | TTG | GAT | CTG | ATG | ACC | TTG | AAG | GGC | GGC | ATT | GAC | 788 |
| Ile | Leu | Pro | Gly | Gly | Leu | Asp | Leu | Met | Thr | Leu | Lys | Gly | Gly | Ile | Asp |  |
|  |  |  |  | 215 |  |  |  |  | 220 |  |  |  |  | 225 |  |  |
| GTG | AGC | CGT | GTG | GCT | GTA | ATG | GGA | CAT | TCA | TTT | GGA | GGG | GCC | ACA | GCT | 836 |
| Val | Ser | Arg | Val | Ala | Val | Met | Gly | His | Ser | Phe | Gly | Gly | Ala | Thr | Ala |  |
|  |  |  | 230 |  |  |  |  | 235 |  |  |  |  | 240 |  |  |  |
| ATT | CTG | GCC | TTG | GCC | AAG | GAG | ATG | CAA | TTT | AGG | TGT | GCT | GTG | GCT | TTG | 884 |
| Ile | Leu | Ala | Leu | Ala | Lys | Glu | Met | Gln | Phe | Arg | Cys | Ala | Val | Ala | Leu |  |
|  |  | 245 |  |  |  |  | 250 |  |  |  |  | 255 |  |  |  |  |
| GAC | GCT | TGG | ATG | TTT | CCT | CTG | GAG | CAT | GAC | TTT | TAC | CCC | ACG | GCC | CGA | 932 |
| Asp | Ala | Trp | Met | Phe | Pro | Leu | Glu | His | Asp | Phe | Tyr | Pro | Thr | Ala | Arg |  |
| 260 |  |  |  |  | 265 |  |  |  |  | 270 |  |  |  |  |  |  |
| GGC | CCT | ATC | TTC | TTT | ATC | AAT | GCT | GAG | AAG | TTC | CAG | ACA | GTG | GAG | ACT | 980 |
| Gly | Pro | Ile | Phe | Phe | Ile | Asn | Ala | Glu | Lys | Phe | Gln | Thr | Val | Glu | Thr |  |
| 275 |  |  |  |  | 280 |  |  |  |  | 285 |  |  |  |  | 290 |  |
| GTC | AAC | TTG | ATG | AAA | AAG | ATT | TGT | GAC | CAG | CAC | CAC | CAA | TCC | AGG | ATC | 1028 |
| Val | Asn | Leu | Met | Lys | Lys | Ile | Cys | Asp | Gln | His | His | Gln | Ser | Arg | Ile |  |
|  |  |  |  | 295 |  |  |  |  | 300 |  |  |  |  | 305 |  |  |
| ATA | ACT | GTC | CTT | GGT | TCT | GTT | CAT | CGG | AGT | CTA | ACC | GAC | TTT | GTT | TTT | 1076 |
| Ile | Thr | Val | Leu | Gly | Ser | Val | His | Arg | Ser | Leu | Thr | Asp | Phe | Val | Phe |  |
|  |  |  | 310 |  |  |  |  | 315 |  |  |  |  | 320 |  |  |  |
| GTG | GCT | GGT | AAC | TGG | ATT | AGT | AAA | TTC | TTC | TCC | AGT | CAC | ACC | CGT | GGA | 1124 |
| Val | Ala | Gly | Asn | Trp | Ile | Ser | Lys | Phe | Phe | Ser | Ser | His | Thr | Arg | Gly |  |
|  |  | 325 |  |  |  |  | 330 |  |  |  |  | 335 |  |  |  |  |
| AGC | TTG | GAC | CCC | TAT | GAA | GGT | CAG | GAG | ACC | GTG | GTG | CGG | GCC | ATG | TTG | 1172 |
| Ser | Leu | Asp | Pro | Tyr | Glu | Gly | Gln | Glu | Thr | Val | Val | Arg | Ala | Met | Leu |  |
|  | 340 |  |  |  |  | 345 |  |  |  |  | 350 |  |  |  |  |  |
| GCC | TTC | CTG | CAG | AAG | CAT | CTT | GAC | CTG | AAA | GAG | GAC | TAT | GAC | CAG | TGG | 1220 |
| Ala | Phe | Leu | Gln | Lys | His | Leu | Asp | Leu | Lys | Glu | Asp | Tyr | Asp | Gln | Trp |  |
| 355 |  |  |  |  | 360 |  |  |  |  | 365 |  |  |  |  | 370 |  |
| AAC | AAC | TTC | ATT | GAA | GGC | ATT | GGC | CCA | TCA | CTG | ACC | CCA | GGG | GCC | CCA | 1268 |
| Asn | Asn | Phe | Ile | Glu | Gly | Ile | Gly | Pro | Ser | Leu | Thr | Pro | Gly | Ala | Pro |  |
|  |  |  |  | 375 |  |  |  |  | 380 |  |  |  |  | 385 |  |  |
| CAC | CAT | CTG | TCC | AGC | CTG | TAGGCACAAC | TGGTCATCTT | GTGGAAGGTC |  |  |  |  |  |  |  | 1316 |
| His | His | Leu | Ser | Ser | Leu |  |  |  |  |  |  |  |  |  |  |  |
|  |  |  | 390 |  |  |  |  |  |  |  |  |  |  |  |  |  |

```
CCTGAGCTGA GTTCCCGTGT GGGGCCTGCC CAGGGATACC CTTGGCCTCC TATCAGGAAG      1376

TGATTGCCAT GACCCTTCTG TGTTGATTGA GAGGATATAA TCACACTGCT GATTGGTAAC      1436

GGGGTACTTG GATTCTCAGA CTTGTCGATC TTAAACTCAT GTTGGGACTT GGGTTCACTT      1496

ACTGATGGGC AAACGGGCAT TCTGAGGACT GAGCCTTAAT GGTATGGAGA ACAAACAGTG      1556

GGATGGGGCT GGGGAAGATC TAAGCCCTAA GCTGGGCACT ATGAGCCCTA TAAACCCAAC      1616

CAGCCAACAC CCTCACCTTG GGCAAGTATG ACTTCTGCAG GTCGACTCT                  1665
```

(2) INFORMATION FOR SEQ ID NO:3:

(i) SEQUENCE CHARACTERISTICS:
        (A) LENGTH: 392 amino acids
        (B) TYPE: amino acid
        (C) STRANDEDNESS: single
        (D) TOPOLOGY: linear (ii) MOLECULE TYPE: peptide (vi) ORIGINAL SOURCE:
        (A) ORGANISM: HUMAN (xi) SEQUENCE DESCRIPTION: SEQ ID NO:3:

```
Met Gly Val Asn Gln Ser Val Gly Phe Pro Pro Val Thr Gly Pro His
  1               5                  10                  15

Leu Val Gly Cys Gly Asp Val Met Glu Gly Gln Asn Leu Gln Gly Ser
                 20                  25                  30

Phe Phe Arg Leu Phe Tyr Pro Cys Gln Lys Ala Glu Glu Thr Met Glu
             35                  40                  45

Gln Pro Leu Trp Ile Pro Arg Tyr Glu Tyr Cys Thr Gly Leu Ala Glu
         50                  55                  60

Tyr Leu Gln Phe Asn Lys Arg Cys Gly Gly Leu Leu Phe Asn Leu Ala
 65                  70                  75                  80

Val Gly Ser Cys Arg Leu Pro Val Ser Trp Asn Gly Pro Phe Lys Thr
                 85                  90                  95

Lys Asp Ser Gly Tyr Pro Leu Ile Ile Phe Ser His Gly Leu Gly Ala
                100                 105                 110

Phe Arg Thr Leu Tyr Ser Ala Phe Cys Met Glu Leu Ala Ser Arg Gly
            115                 120                 125

Phe Val Val Ala Val Pro Glu His Arg Asp Arg Ser Ala Ala Thr Thr
        130                 135                 140

Tyr Phe Cys Lys Gln Ala Pro Glu Glu Asn Gln Pro Thr Asn Glu Ser
145                 150                 155                 160

Leu Gln Glu Glu Trp Ile Pro Phe Arg Arg Val Glu Glu Gly Glu Lys
                165                 170                 175

Glu Phe His Val Arg Asn Pro Gln Val His Gln Arg Val Ser Glu Cys
                180                 185                 190

Leu Arg Val Leu Lys Ile Leu Gln Glu Val Thr Ala Gly Gln Thr Val
            195                 200                 205

Phe Asn Ile Leu Pro Gly Gly Leu Asp Leu Met Thr Leu Lys Gly Asn
        210                 215                 220

Ile Asp Met Ser Arg Val Ala Val Met Gly His Ser Phe Gly Gly Ala
225                 230                 235                 240

Thr Ala Ile Leu Ala Leu Ala Lys Glu Thr Gln Phe Arg Cys Ala Val
                245                 250                 255

Ala Leu Asp Ala Trp Met Phe Pro Leu Glu Arg Asp Phe Tyr Pro Lys
                260                 265                 270

Ala Arg Gly Pro Val Phe Phe Ile Asn Thr Glu Lys Phe Gln Thr Met
            275                 280                 285

Glu Ser Val Asn Leu Met Lys Lys Ile Cys Ala Gln His Glu Gln Ser
        290                 295                 300

Arg Ile Ile Thr Val Leu Gly Ser Val His Arg Ser Gln Thr Asp Phe
305                 310                 315                 320

Ala Phe Val Thr Gly Asn Leu Ile Gly Lys Phe Phe Ser Thr Glu Thr
                325                 330                 335

Arg Gly Ser Leu Asp Pro Tyr Glu Gly Gln Glu Val Met Val Arg Ala
```

```
                340             345             350
Met Leu Ala Phe Leu Gln Lys His Leu Asp Leu Lys Glu Asp Tyr Asn
            355             360             365

Gln Trp Asn Asn Leu Ile Glu Gly Ile Gly Pro Ser Leu Thr Pro Gly
    370             375             380

Ala Pro His His Leu Ser Ser Leu
385             390
```

(2) INFORMATION FOR SEQ ID NO:4:

(i) SEQUENCE CHARACTERISTICS:
        (A) LENGTH: 2559 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: HUMAN (ix) FEATURE:
        (A) NAME/KEY: CDS
        (B) LOCATION: 216..1392

(xi) SEQUENCE DESCRIPTION: SEQ ID NO:4:

```
GCAGGTCTCG ACCCACGCGT CCGCGGACGC GTGGGCGAGA AGTGCTTCCA AGCGTCCATT      60

TTGAGCCTTG AAACTACGA CGACCAAAGG GCCACGGGTT CCTGGGTCGT TTCTCATTTC     120

CGTCGAGTTA AACGTCTGGG GCTGCTTCTG AGGAATCAGC TTGGCTGGCC AGCAAGTTCA    180

GCTCCGGCAA GTCATTTGAT TCACCCGGTG ATGAA ATG GGG GTC AAC CAG TCT       233
                                       Met Gly Val Asn Gln Ser
                                         1               5

GTG GGC TTT CCA CCT GTC ACA GGA CCC CAC CTC GTA GGC TGT GGG GAT      281
Val Gly Phe Pro Pro Val Thr Gly Pro His Leu Val Gly Cys Gly Asp
            10              15              20

GTG ATG GAG GGT CAG AAT CTC CAG GGG AGC TTC TTT CGA CTC TTC TAC      329
Val Met Glu Gly Gln Asn Leu Gln Gly Ser Phe Phe Arg Leu Phe Tyr
        25              30              35

CCC TGC CAA AAG GCA GAG GAG ACC ATG GAG CAG CCC CTG TGG ATT CCC      377
Pro Cys Gln Lys Ala Glu Glu Thr Met Glu Gln Pro Leu Trp Ile Pro
    40              45              50

CGC TAT GAG TAC TGC ACT GGC CTG GCC GAG TAC CTG CAG TTT AAT AAG      425
Arg Tyr Glu Tyr Cys Thr Gly Leu Ala Glu Tyr Leu Gln Phe Asn Lys
55              60              65              70

CGC TGC GGG GGC TTG CTG TTC AAC CTG GCG GTG GGA TCT TGT CGC CTG      473
Arg Cys Gly Gly Leu Leu Phe Asn Leu Ala Val Gly Ser Cys Arg Leu
            75              80              85

CCT GTT AGC TGG AAT GGC CCC TTT AAG ACA AAG GAC TCT GGA TAC CCC      521
Pro Val Ser Trp Asn Gly Pro Phe Lys Thr Lys Asp Ser Gly Tyr Pro
        90              95              100

TTG ATC ATC TTC TCC CAT GGC CTA GGA GCC TTC AGG ACT TTG TAT TCA      569
Leu Ile Ile Phe Ser His Gly Leu Gly Ala Phe Arg Thr Leu Tyr Ser
    105             110             115

GCC TTC TGC ATG GAG CTG GCC TCA CGT GGC TTT GTG GTT GCT GTG CCA      617
Ala Phe Cys Met Glu Leu Ala Ser Arg Gly Phe Val Val Ala Val Pro
120             125             130

GAG CAC AGG GAC CGG TCA GCG GCA ACC ACC TAT TTC TGC AAG CAG GCC      665
Glu His Arg Asp Arg Ser Ala Ala Thr Thr Tyr Phe Cys Lys Gln Ala
135             140             145             150

CCA GAA GAG AAC CAG CCC ACC AAT GAA TCG CTG CAG GAG GAA TGG ATC      713
Pro Glu Glu Asn Gln Pro Thr Asn Glu Ser Leu Gln Glu Glu Trp Ile
```

-continued

```
                 155                 160                     165
CCT TTC CGT CGA GTT GAG GAA GGG GAG AAG GAA TTT CAT GTT CGG AAT          761
Pro Phe Arg Arg Val Glu Glu Gly Glu Lys Glu Phe His Val Arg Asn
            170                 175                 180

CCC CAG GTG CAT CAG CGG GTA AGC GAG TGT TTA CGG GTG TTG AAG ATC          809
Pro Gln Val His Gln Arg Val Ser Glu Cys Leu Arg Val Leu Lys Ile
                185                 190                 195

CTG CAA GAG GTC ACT GCT GGG CAG ACT GTC TTC AAC ATC TTG CCT GGT          857
Leu Gln Glu Val Thr Ala Gly Gln Thr Val Phe Asn Ile Leu Pro Gly
    200                 205                 210

GGC TTG GAT CTG ATG ACT TTG AAG GGC AAC ATT GAC ATG AGC CGT GTG          905
Gly Leu Asp Leu Met Thr Leu Lys Gly Asn Ile Asp Met Ser Arg Val
215                 220                 225                 230

GCT GTG ATG GGA CAT TCA TTT GGA GGG GCC ACA GCT ATT CTG GCT TTG          953
Ala Val Met Gly His Ser Phe Gly Gly Ala Thr Ala Ile Leu Ala Leu
                235                 240                 245

GCC AAG GAG ACC CAA TTT CGG TGT GCG GTG GCT CTG GAT GCT TGG ATG         1001
Ala Lys Glu Thr Gln Phe Arg Cys Ala Val Ala Leu Asp Ala Trp Met
            250                 255                 260

TTT CCT CTG GAA CGT GAC TTT TAC CCC AAG GCC CGA GGA CCT GTG TTC         1049
Phe Pro Leu Glu Arg Asp Phe Tyr Pro Lys Ala Arg Gly Pro Val Phe
                265                 270                 275

TTT ATC AAT ACT GAG AAA TTC CAG ACA ATG GAG AGT GTC AAT TTG ATG         1097
Phe Ile Asn Thr Glu Lys Phe Gln Thr Met Glu Ser Val Asn Leu Met
    280                 285                 290

AAG AAG ATA TGT GCC CAG CAT GAA CAG TCT AGG ATC ATA ACC GTT CTT         1145
Lys Lys Ile Cys Ala Gln His Glu Gln Ser Arg Ile Ile Thr Val Leu
295                 300                 305                 310

GGT TCT GTT CAT CGG AGT CAA ACT GAC TTT GCT TTT GTG ACT GGC AAC         1193
Gly Ser Val His Arg Ser Gln Thr Asp Phe Ala Phe Val Thr Gly Asn
                315                 320                 325

TTG ATT GGT AAA TTC TTC TCC ACT GAA ACC CGT GGG AGC CTG GAC CCC         1241
Leu Ile Gly Lys Phe Phe Ser Thr Glu Thr Arg Gly Ser Leu Asp Pro
            330                 335                 340

TAT GAA GGG CAG GAG GTT ATG GTA CGG GCC ATG TTG GCC TTC CTG CAG         1289
Tyr Glu Gly Gln Glu Val Met Val Arg Ala Met Leu Ala Phe Leu Gln
                345                 350                 355

AAG CAC CTC GAC CTG AAA GAA GAC TAT AAT CAA TGG AAC AAC CTT ATT         1337
Lys His Leu Asp Leu Lys Glu Asp Tyr Asn Gln Trp Asn Asn Leu Ile
    360                 365                 370

GAA GGC ATT GGA CCG TCG CTC ACC CCA GGG GCC CCC CAC CAT CTG TCC         1385
Glu Gly Ile Gly Pro Ser Leu Thr Pro Gly Ala Pro His His Leu Ser
375                 380                 385                 390

AGC CTG T AGGCACAACT GGCCATTTGT AAAGTCACTT CAGCCAAGTT TTCATTTGGG        1442
Ser Leu

AGCTACCCAA GGGCACCCAT GAGCTCCTAT CAAGAAGTGA TCAACGTGAC CCCTTTTCAC       1502

AGATTGAAAG GTGTAATCAC ACTGCTGCTT GGATAACTGG GTACTTTGAT CTTAGATTTG       1562

ATCTTAAAAT CACTTTGGGA CTGGGATCCC TTGCTGATTG ACAAACAGAC TTTCTGGGAC       1622

CTTGATGGAG TGGGGAACAA GCAGTAGAGT GGGACTGGGG GAGACCCAGG CCCCGGGCTG       1682

AGCACTGTGA GGCCTGGATG TGAAGACTCA GCCCAGCGAA GCTCATTCCC TTACCCCCGG       1742

CCAGTGCTGC TGCTTCAGTG GAAGAGATGA AGCCAAAGGA CAGAATGAAA ATCCCTACCT       1802

TCAGAGACTC TAGCCCAGCC CAACACCATC TCTTCCTACC TCTCAGCCTT CTCCCTCCCC       1862

AGGGCCACTT GTTGAAGTCT GAGCACTTTA TGTAAATTTC TAGGTGTGAG CCGTGATCAC       1922

ATTTTCTATT TATTTCCAAG TCTTCTCATT GTATGGAACA TAGTACTACT TATACTTACA       1982
```

| | | | | |
|---|---|---|---|---|
| GTAGTAAGTT | ATACTTGTGA | GCCCACAGAG | TGGCAGACAG | CATGGCTCTC ACAGCACAGG | 2042 |
| GAGAAAAACT | GAGGTACACA | GAGGTACCTC | AGAAGCTCTG | GATGTCTTTG GGGGTTTTGC | 2102 |
| TAAGTGTATC | TTGATAGGAA | ACAACAAAAG | CAGGTTGAGA | TGGGGAAGAT GACAGAACAA | 2162 |
| CAGTGTTAAA | TGGCCATTTG | CACAGGCCTT | TGCCACAACA | GAGAAGTAGT TTGGTCAGCT | 2222 |
| AAAACTCAGC | TGCAGCCTGG | ACAGTAGAGC | GAGACCCCAT | CTTAAAAATA AAGAAGGCTG | 2282 |
| GGCGTGGTGG | CTCATGCCTG | TAATCCCAGC | ACTTTGGGAG | GCCAAGGCAG GCAGATCACT | 2342 |
| TAAGGCCAGG | AGTTCAAGAC | CACCTGGCCA | ACATGGTGAA | ACCCCGTCTC TACTAAAAAT | 2402 |
| ACAAAAAATT | AGCCTGGCGT | AATGGCAGGC | GCCTATAATC | CCAGCTACTC AGGAGGCTGA | 2462 |
| AGCAGAAGAA | TCACTTGAAC | CTAGGAGGCG | GAGGTTGCAG | TGAGTCAAGA TCGCGCCACT | 2522 |
| GCACTCCAGC | CTGGGTGACA | GAGCAAGACT | CTGTCTT | | 2559 |

PLATELET ACTIVATING FACTOR ACETYLHYDROLASE, AND GENE THEREOF

This application is a division of 08/886,152, filed Jun. 30, 1997, now 5,880,273.

BACKGROUND OF THE INVENTION a) Field of the Invention

This invention relates to a novel platelet activating factor acetylhydrolase, and a gene encoding the same.

b) Description of the Related Art

A platelet activating factor acetylhydrolase is an enzyme, which acts on a platelet activating factor (hereinafter abbreviated as "PAF") and eliminates its 2-acetyl group to deprive PAF of its activity. Since PAF is a mediator for inflammation which causes defluxion of tissue fluid through finer vessels, vasodilation, smooth muscle contraction, endothelial adhesion, activation of neutrophils, macrophages or eosinophilic leukocytes, or the like, PAF acetylhydrolase is usable as a preventive or therapeutic for various diseases caused by PAF.

Some reports have been made about PAF acetylhydrolase to date. For its use as a medicine, however, there is an outstanding desire for the provision of a PAF acetylhydrolase having higher purity and stronger action compared with conventional PAF acetylhydrolase. Further, from the viewpoint of safety, PAF acetylhydrolase derived form human being instead of an animal is desired.

SUMMARY OF THE INVENTION

With the foregoing in view, the present invention has as a primary object the provision of PAF acetylhydrolase which can fulfill the above-described desires.

Interested in the wide-spread distribution of PAF acetylhydrolase in animal organs such as the brain and kidneys, the present inventors chose the bovine liver as a source, and by various isolation and purification procedures, progressively increased the purity of PAF acetylhydrolase while placing a focus on its enzymatic activity. As a result, the present inventors have succeeded in obtaining bovine PAF acetylhydrolase as a pure product and further in determining its amino acid sequence. In addition, from the amino acid sequence of the PAF acetylhydrolase, a gene encoding the enzyme has been found by methods known per se in the art.

Moreover, using the bovine PAF acetylhydrolase cDNA, the present inventors have also succeeded in identifying the human PAF acetylhydrolase cDNA.

The present invention has been completed based on these findings, and provides a human PAF acetylhydrolase, which plays an important role as a PAF-inhibiting substance, and also a gene which encodes the enzyme and is important for the synthesis of the enzyme by genetic engineering.

The human PAF acetylhydrolase according to the present invention selectively degrades PAF and hence, is usable as medicines or biochemical reagents for the prevention and treatment of diseases caused by PAF, for example, diseases such as asthma, exudative tympanitis, hemorrhagic colitis and adult respiratory distress syndrome.

DETAILED DESCRIPTION OF THE INVENTION AND PREFERRED EMBODIMENTS

The human PAF acetylhydrolase according to the present invention can be prepared as will be described next. PAF acetylhydrolase is first collected from an animal. From the PAF acetylhydrolase, the animal PAF acetylhydrolase cDNA is determined. Using the animal PAF acetylhydrolase cDNA, the human PAF acetylhydrolase cDNA is detected from a human gene library. The human PAF acetylhydrolase cDNA is inserted in an appropriate vector and then cultures in an adequate host organism, whereby the human PAF acetylhydrolase is obtained.

Upon practice of the present invention, it is first necessary to obtain animal PAF acetylhydrolase from an organ of an animal such as the brain, liver or kidneys by purifying it through repetitions of known isolation and purification procedures while using PAF acetylhydrolase activity as an index. A description will hereinafter be made of a process for obtaining PAF acetylhydrolase by using a bovine liver as an example.

As the bovine liver to be used as a source, one obtained from a bovine immediately after its slaughter is preferred.

After the bovine liver is first washed with an appropriate buffer (for example, 10 mM Tris-HCl buffer containing 250 mM sucrose and 1 mM EDTA and having a pH of 7.4), it is homogenized with the same buffer. The homogenate is then centrifuged to obtain a soluble fraction.

Making combined use of hydrophobic chromatography, ion exchange chromatography, adsorption chromatography, gel filtration chromatography and the like, the soluble fraction is purified until a single peak is observed by Mono Q FPLC, so that PAF acetyl hydrolase can be obtained.

Incidentally, PAF acetylhydrolase activity which is used as an index for the selective collection of the PAF-acetylhydrolase-containing fraction can be determined, for example, by the method disclosed in Japanese Patent Application Laid-Open (Kokai) No. HEI 7-39373.

With respect to the bovine PAF acetylhydrolase obtained in the above-described manner, its amino acid sequence was investigated by a method known per se in the art. As a result, the amino acid sequence has been found to be represented by the following formula (III) (SEQ ID NO:1):

Met Gly Val Asn Gln Ser Val Ser Phe Pro Pro Val Thr Gly
Pro His Leu Val Gly Cys Gly Asp Val Met Glu Gly Gln
Ser Leu Gln Gly Ser Phe Phe Arg Leu Phe Tyr Pro Cys
Gln Glu Ala Glu Glu Thr Ser Glu Gln Pro Leu Trp Ile
Pro Arg Tyr Glu Tyr Cys Ala Gly Leu Ala Glu Tyr Leu
Lys Phe Asn Lys Arg Trp Gly Gly Leu Leu Phe Asn Leu
Gly Val Gly Ser Cys Arg Leu Pro Val Ser Trp Asn Gly
Pro Phe Lys Thr Lys Asp Ser Gly Tyr Pro Leu Ile Ile
Phe Ser His Gly Met Gly Ala Phe Arg Thr Val Tyr Ser
Ala Phe Cys Met Glu Leu Ala Ser Arg Gly Phe Val Val
Ala Val Pro Glu His Arg Asp Gly Ser Ala Ala Ala Thr
Cys Phe Cys Lys Gln Thr Pro Glu Glu Asn Gln Pro Asp
Asn Glu Ala Leu Lys Glu Glu Trp Ile Pro His Arg Gln
Ile Glu Glu Gly Glu Lys Glu Phe Tyr Val Arg Asn Tyr
Gln Val His Gln Arg Val Ser Glu Cys Val Arg Val Leu
Lys Ile Leu Gln Glu Val Thr Ala Gly Gln Ala Val Leu
Asn Ile Leu Pro Gly Gly Leu Asp Leu Met Thr Leu Lys
Gly Gly Ile Asp Val Ser Arg Val Ala Val Met Gly His
Ser Phe Gly Gly Ala Thr Ala Ile Leu Ala Leu Ala Lys
Glu Met Gln Phe Arg Cys Ala Val Ala Leu Asp Ala Trp
Met Phe Pro Leu Glu His Asp Phe Tyr Pro Thr Ala Arg
Gly Pro Ile Phe Phe Ile Asn Ala Glu Lys Phe Gln Thr
Val Glu Thr Val Asn Leu Met Lys Lys Ile Cys Asp Gln
His His Gln Ser Arg Ile Ile Thr Val Leu Gly Ser Val His
Arg Ser Leu Thr Asp Phe Val Phe Val Ala Gly Asn Trp
Ile Ser Lys Phe Phe Ser Ser His Thr Arg Gly Ser Leu
Asp Pro Tyr Glu Gly Gln Glu Thr Val Val Arg Ala Met
Leu Ala Phe Leu Gln Lys His Leu Asp Leu Lys Glu Asp

Tyr Asp Gln Trp Asn Ash Phe Ile Glu Gly Ile Gly Pro Ser Leu Thr Pro Gly Ala Pro His His Leu Ser Ser Leu (III)

Further, from the peptide sequence of the bovine PAF acetylhydrolase of the formula (III), a gene encoding the enzyme was determined by a method known per se in the art. The gene (hereinafter called the "bovine PAF acetylhydrolase cDNA") has been found to be identified by the following formula (IV) (SEQ ID NO:2):

GTCGACCCACGCGTCCGAGTTGACCGT CTGGGCTGTTTCTGAGGGTCAACGT-GACTCGCCGTCAAGTTCAGCCACTGC-CCAAGTCGT CGTTCAGTTCAGTTGGTTATGAG ATG GGG GTC AAC CAG TCT GTG AGC TTC CCA CCC GTC ACG GGA CCC CAC CTC GTA GGC TGT GGG GAT GTG ATG GAG GGT CAG AGC CTC CAG GGC AGC TTC TTT CGA CTG TTC TAC CCG TGC CAA GAG GCA GAG GAG ACC TCG GAG CAG CCC CTG TGG ATT CCC CGC TAT GAG TAC TGC GCT GGC CTG GCC GAA TAC CTA AAG TTT AAT AAG CGC TGG GGG GGG TTA CTG TTC AAC CTG GGT GTG GGA TCT TGT CGC CTG CCT GTT AGC TGG AAT GGC CCC TTT AAA ACA AAG GAC TCT GGA TAC CCC TTG ATC ATC TTC TCT CAT GGC ATG GGA GCC TTC AGG ACA GTG TAT TCA GCC TTC TGC ATG GAG CTG GCT TCT CGT GGC TTT GTG GTT GCT GTA CCA GAG CAC AGG GAT GGG TCA GCT GCG GCC ACC TGT TTC TGC AAG CAG ACC CCA GAG GAG AAC CAG CCT GAC AAT GAG GCC CTG AAG GAG GAA TGG ATC CCC CAC CGT CAA ATT GAG GAA GGG GAG AAG GAA TTC TAT GTT CGG AAC TAC CAG GTG CAT CAG AGG GTG AGC GAG TGT GTG AGG GTG TTG AAG ATC CTA CAA GAG GTC ACT GCT GGG CAG GCC GTT CTC AAC ATC TTG CCT GGC GGA TTG GAT CTG ATG ACC TTG AAG GGC GGC ATT GAC GTG AGC CGT GTG GCT GTA ATG GGA CAT TCA TTT GGA GGG GCC ACA GCT ATT CTG GCC TTG GCC AAG GAG ATG CAA TTT AGG TGT GCT GTG GCT TTG GAC GCT TGG ATG TTT CCT CTG GAG CAT GAC TTT TAC CCC ACG GCC CGA GGC CCT ATC TTC TTT ATC AAT GCT GAG AAG TTC CAG ACA GTG GAG ACT GTC AAC TTG ATG AAA AAG ATT TGT GAC CAG CAC CAC CAA TCC AGG ATC ATA ACT GTC CTT GGT TCT GTT CAT CGG AGT CTA ACC GAC TTT GTT TTT GTG GCT GGT AAC TGG ATT AGT AAA TTC TTC TCC AGT CAC ACC CGT GGA AGC TTG GAC CCC TAT GAA GGT CAG GAG ACC GTG GTG CGG GCC ATG TTG GCC TTC CTG CAG AAG CAT CTT GAC CTG AAA GAG GAC TAT GAC CAG TGG AAC AAC TTC ATT GAA GGC ATT GGC CCA TCA CTG ACC CCA GGG GCC CCA CAC CAT CTG TCC AGC CTG TAG GCACAACTGGTCATCTTGTG-GAAG GTCCCTGAGCTGAGTTCCCGT-GTGGGGCCTGCCCAGGGATACCCTTGGC-CTCCTATCAGG AAGTGATTGCCATGACCCTT-CTGTGTTGATTGAGAGGATATAATCA-CACTGCTGATTGGT AACGGGGTACTTGGAT-TCTCAGACTTGTCGATCTTAAACTCAT-GTTGGGACTTGGGTTCA CTTACTGATGGGC-AAACGGGCATTCTGAGGACTGAGCCTTAATGG-TATGGAGAACAAACAGTGGGATGGGGCT-GGGGAAGATCTAAGCCCTAAGCTGGGCACTAT-GAGCCCTATAAACCC AACCAGCCAACACCCT-CACCTTGGGCAAGTATGACTTCTGCAG-GTCGACTCT (IV)

To obtain human PAF acetylhydrolase from the bovine PAF acetylhydrolase CDNA obtained as described above, the human gene library is screened by a method known per se in the art while using the bovine PAF acetylhydrolase cDNA as a template.

Described specifically, the bovine PAF acetylhydrolase cDNA is labeled, for example, by incorporating fluorescein-12-dUTP through PCR. By the colony hybridization technique that selects each positive colony by ECL (Enhanced Chemiluminescence; Amersham K. K.), colonies containing the human PAF acetylhydrolase cDNA can be obtained.

The human PAF acetylhydrolase cDNA obtained as described above has been found to be identified by the following formula (II) (SEQ ID NO:4):

GCAGGTCTCGACCCACGCGTCCGCG-GACGCGTGGG CGAGAAGTGCTTCCAAGCGTC-CATTTTGAGCCTTGGAAACTACGACGAC-CAAAGGGCCAC GGGTTCCTGGGTCGTTT-CTCATTTCCGTCGAGTTAAACGTCTGGGG-CTGCTTCTGAGGAA TCAGCTTGGCTGGCCAG-CAAGTTCAGCTCCGGCAAGTCATTTGAT-TCACCCGGTGATGAA ATG GGG GTC AAC CAG TCT GTG GGC TTT CCA CCT GTC ACA GGA CCC CAC CTC GTA GGC TGT GGG GAT GTG ATG GAG GGT CAG AAT CTC CAG GGG AGC TTC TTT CGA CTC TTC TAC CCC TGC CAA AAG GCA GAG GAG ACC ATG GAG CAG CCC CTG TGG ATT CCC CGC TAT GAG TAC TGC ACT GGC CTG GCC GAG TAC CTG CAG TTT AAT AAG CGC TGC GGG GGC TTG CTG TTC AAC CTG GCG GTG GGA TCT TGT CGC CTG CCT GTT AGC TGG AAT GGC CCC TTT AAG ACA AAG GAC TCT GGA TAC CCC TTG ATC ATC TTC TCC CAT GGC CTA GGA GCC TTC AGG ACT TTG TAT TCA GCC TTC TGC ATG GAG CTG GCC TCA CGT GGC TTT GTG GTT GCT GTG CCA GAG CAC AGG GAC CGG TCA GCG GCA ACC ACC TAT TTC TGC AAG CAG GCC CCA GAA GAG AAC CAG CCC ACC AAT GAA TCG CTG CAG GAG GAA TGG ATC CCT TTC CGT CGA GTT GAG GAA GGG GAG AAG GAA TTT CAT GTT CGG AAT CCC CAG GTG CAT CAG CGG GTA AGC GAG TGT TTA CGG GTG TTG AAG ATC CTG CAA GAG GTC ACT GCT GGG CAG ACT GTC TTC AAC ATC TTG CCT GGT GGC TTG GAT CTG ATG ACT TTG AAG GGC AAC ATT GAC ATG AGC CGT GTG GCT GTG ATG GGA CAT TCA TTT GGA GGG GCC ACA GCT ATT CTG GCT TTG GCC AAG GAG ACC CAA TTT CGG TGT GCG GTG GCT CTG GAT GCT TGG ATG TTT CCT CTG GAA CGT GAC TTT TAC CCC AAG GCC CGA GGA CCT GTG TTC TTT ATC AAT ACT GAG AAA TTC CAG ACA ATG GAG AGT GTC AAT TTG ATG AAG AAG ATA TGT GCC CAG CAT GAA CAG TCT AGG ATC ATA ACC GTT CTT GGT TCT GTT CAT CGG AGT CAA ACT GAC TTT GCT TTT GTG ACT GGC AAC TTG ATT GGT AAA TTC TTC TCC ACT GAA ACC CGT GGG AGC CTG GAC CCC TAT GAA GGG CAG GAG GTT ATG GTA CGG GCC ATG TTG GCC TTC CTG CAG AAG CAC CTC GAC CTG AAA GAA GAC TAT AAT CAA TGG AAC AAC CTT ATT GAA GGC ATT GGA CCG TCG CTC ACC CCA GGG GCC CCC CAC CAT CTG TCC AGC CTG TAG GCACAACTGGCCATTTG-TAAAGTCACTTCAGCCAAGTTTTCATTTGGG AGCTACCCAAGGGCACCCATGAGCTCCTATCA-AGAAGTGATCAACGTGACCCC- TTTTCAC AGATTGAAAGGTGTAATCACACTGCT-GCTTGGATAACTGGGTACTTTGATCTTA-

GATTTG ATCTTAAAATCACTTTGGGACTGGG-
ATCCCTTGCTGATTGACAAACAGACTTT-
CTGGGAC CTTGATGGAGTGGGGAACAAGCAG-
TAGAGTGGGACTGGGGGAGACCCAGGC-
CCCGGGCTG AGCACTGTGAGGCCTGGAT-
GTGAA GACTCAGCCAGCGAAGCTCATT-
CCCTTACCCCCGG CCAGTGCTGCTGCT-
TCAGTGGAAGAGATGAAGCCAAAGGACA-
GAATGAAAATCCCTACCT TCAGAGACTCTA-
GCCCAGCCCAACACCATCTCTTCCTACCTCTC-
AGCCTTCTCCCTCCCC AGGGCCACTTGT-
TGAAGTCTGAGCACTTTATGTAAATTT
CTAGGTGTGAGCCGTGATCACATTTTCTATTTA-
TTTCCAAGTCTTCTCATTGTATGGAACATAG-
TACTACTTATACTTACA GTAGTAAGTTATACT-
TGTGAGCCCACAGAGTGGCAGACAG-
CATGGCTCTCACAGCACAGG GAGAAAAACT-
GAGGTACACAGAGGTACCTCAGAAGCTCTGG-
ATGTCTTTGGGGGTTTTGC TAAGTGTAT-
CTTGATAGGAAACAACAAAAGCAGGTTG-
AGATGGGGAAGATGACAGAACAA CAGTGT-
TAAATGGCCATTTGCACAGGCCTTTGC-
CACAACAGAGAAGTAGTTTGGTCAGCT
AAAACTCAGCTGCAGCCTGGACAGTA-
GAGCGAGACCCCATCTTAAAAATAAA-
GAAGGCTG GGCGTGGTGGCTCATGCCTG-
TAAT CCCAGCACTTTGGGAGGCCAAGGCAGG-
CAGATCACT TAAGGCCAGGAGTTCAAGA-
CCACC TGGCCAACATGGTGAAACCCCG-
TCTCTACTAAAAAT ACAAAAAATTAGCCTG-
GCGT AATGGCAGGCGCCTATAATCCCA-
GCTACTCAGGAGGCTGA AGCAGAAGAAT-
CACTTGAACCTAGGAGGCGGAGGTTG-
CAGTGAGTCAAGATCGCGCCACT GCACTC-
CAGCCTGGGTGACAGAGCAAGACTCTGTCTT
(II)

Following conventional procedures, the human PAF acetylhydrolase cDNA obtained as described above is next introduced in an appropriate vector plasmid, and host cells such as mammal cells are then transformed by a commonly-employed recombinant DNA technique to express the human PAF acetylhydrolase. The expression of the human PAF acetylhydrolase can be confirmed by a western blot technique which makes use of an anti-human PAF acetylhydrolase antibody. The introduction into the plasmid, the establishment of the transformed strain, the culture of the strain and the like can be conducted by the general recombinant DNA technology.

From expression systems known to artisans, a suitable expression system can be selected for use in the present invention. It is possible to improve the efficiency of secretion and the level of expression by adding or improving a signal sequence and/or choosing an appropriate host. Although no particular limitation is imposed on host cells, illustrative examples include cultured cells of bacteria, yeasts, other fungi, human and other animals, and cultured cells of plants. Namely, the polynucleotide according to the present invention is inserted in a suitable expression vector, for example, pUC-PL-cl vector, the expression vector is introduced in adequate host cells, for example, *E. Coli* W3110 or the like, and the host cells are then cultured. The target human PAF acetylhydrolase can thereafter be collected as a protein from the thus-obtained cultured matter (cells or culture medium).

As the host, a procaryote or an eucaryote can be used. Usable examples of the procaryote include bacteria, especially *Escherichia coli* and Bacillus bacteria, for example, *B. subtilis*. On the other hand, usable examples of the eucaryote include eucaryotic microorganisms such as yeasts, for example, Saccharomyces yeasts, especially *S. Servisiae*; insect cells such as armyworm (*Spodoptera Frugiperda*) cells and silkworm (*Bombyx mori*) cells; and animal cells such as human cells, monkey cells and mouse cells, especially monkey cells, for example, COS1 and COS 7.

Usable examples of the expression vector include plasmids, phages, phargemids, viruses [baculoviruses (for insect cells), vaccinia viruses (for animal cells)]. The promoter in the expression vector is selected depending on the host cells. For examples, lac promoters, trp promoters, trc promoters and the like can be used as promoters for bacteria; and adh 1 promoters, pgk promoters and the like can be used as promoters for yeasts. Further, baculovirus polyhedrin promoters can be mentioned as promoters for insects; and early and late promoters of Simian virus 40 (SV40) can be mentioned as promoters for animal cells.

When an enhancer is used, for example, the enhancer of SV40 is inserted either upstream or downstream of the gene.

The transformation of the host by the expression vector can be conducted by a common method known per se in the art. Such methods are disclosed, for example, in "Current Protocols in Molecular Biology", John Wiley & Sons, Inc.

The culture of the transformants can also be conducted by a usual method. The purification of the human PAF acetylhydrolase from the cultured matter can be conducted following procedures commonly employed for the isolation and purification of proteins, for example, by ultrafiltration and/or one or more of various column chromatographic procedures, for example, chromatography making use of "Sepharose".

In the above-described manner, the human PAF acetylhydrolase can be advantageously obtained. The human PAF acetylhydrolase according to the present invention is represented by the following formula (I) (SEQ ID NO:3):

Met Gly Val Asn Gln Ser Val Gly Phe Pro Pro Val Thr Gly
Pro His Leu Val Gly Cys Gly Asp Val Met Glu Gly Gln
Asn Leu Gln Gly Ser Phe Arg Leu Phe Tyr Pro Cys
Gln Lys Ala Glu Glu Thr Met Glu Gln Pro Leu Trp Ile
Pro Arg Tyr Glu Tyr Cys Thr Gly Leu Ala Glu Tyr Leu
Gln Phe Asn Lys Arg Cys Gly Gly Leu Leu Phe Asn
Leu Ala Val Gly Ser Cys Arg Leu Pro Val Ser Trp Asn
Gly Pro Phe Lys Thr Lys Asp Ser Gly Tyr Pro Leu Ile
Ile Phe Ser His Gly Leu Gly Ala Phe Arg Thr Leu Tyr
Ser Ala Phe Cys Met Glu Leu Ala Ser Arg Gly Phe Val
Val Ala Val Pro Glu His Arg Asp Arg Ser Ala Ala Thr
Thr Tyr Phe Cys Lys Gln Ala Pro Glu Glu Asn Gln Pro
Thr Asn Glu Ser Leu Gln Glu Glu Trp Ile Pro Phe Arg
Arg Val Glu Glu Gly Glu Lys Glu Phe His Val Arg Asn
Pro Gln Val His Gln Arg Val Ser Glu Cys Leu Arg Val
Leu Lys Ile Leu Gln Glu Val Thr Ala Gly Gln Thr Val
Phe Asn Ile Leu Pro Gly Gly Leu Asp Leu Met Thr Leu
Lys Gly Asn Ile Asp Met Ser Arg Val Ala Val Met Gly
His Ser Phe Gly Gly Ala Thr Ala Ile Leu Ala Leu Ala
Lys Glu Thr Gln Phe Arg Cys Ala Val Ala Leu Asp Ala
Trp Met Phe Pro Leu Glu Arg Asp Phe Tyr Pro Lys Ala
Arg Gly Pro Val Phe Phe Ile Asn Thr Glu Lys Phe Gln
Thr Met Glu Ser Val Asn Leu Met Lys Lys Ile Cys Ala
Gln His Glu Gln Ser Arg Ile Ile Thr Val Leu Gly Ser Val
His Arg Ser Gln Thr Asp Phe Ala Phe Val Thr Gly Asn
Leu Ile Gly Lys PIle Phe Ser Thr Glu Thr Arg Gly Ser
Leu Asp Pro Tyr Glu Gly Gln Glu Val Met Val Arg Ala
Met Leu Ala Phe Leu Gln Lys His Leu Asp Leu Lys Glu
Asp Tyr Asn Gln Trp Asn Asn Leu Ile Glu Gly Ile Gly
Pro Ser Leu Thr Pro Gly Ala Pro His His Leu Ser Ser
Leu (I)

The human PAF acetylhydrolase selectively degrades PAF and oxidized phospholipids and has physiologically active effects such anti-inflammatory effects.

Needless to say, the human PAF acetylhydrolase according to the present invention is not limited to the peptide of the formula (I) (SEQ ID NO:3) but includes peptides having homology therewith, namely, peptides having the same function as the peptide represented by the formula (I) (SEQ ID NO:3) despite substitution, deletion, addition or the like of amino acids at parts of their sequences.

The bovine PAF acetylhydrolase represented by the formula (III) (SEQ ID NO:4) may be contemplated to be available by gene manipulation in a similar manner as the human PAF acetylhydrolase. As a matter of fact, however, the bovine PAF acetylhydrolase cannot be obtained unless eucaryotic host cells are used.

To obtain the bovine PAF acetylhydrolase by gene manipulation, it is therefore necessary to employ as host cells those derived from an eucaryote and to select and use a vector compatible with the host cells.

An antibody against the human PAF acetylhydrolase or bovine PAF acetylhydrolase (which may hereinafter be collectively called the "PAF acetylhydrolase") according to the present invention can also be obtained following usual procedures.

Described specifically, the antibody can be obtained by sensitizing an animal such as a rabbit with the PAF acetylhydrolase, separating its serum and, if necessary, purifying an immunoglobulin fraction from the serum. To enhance the sensitizing ability of the enzyme in this case, the enzyme in a form bound on a carrier protein such as bovine serum albumin (BSA) or methyl BSA may be used as an immunogen.

Upon sensitizing an animal, the enzyme can also be used together with Freund's complete adjuvant (FCA) or Freund's incomplete adjuvant (FICA) to increase the production of the antibody. It is desired to conduct the sensitization of the animal twice or more. The frequency of sensitization can be determined while checking the antibody titer of the serum by test sampling of blood. The whole blood of an immune animal may be used by slaughtering it as needed. As an alternative, an immune animal may be subjected to booster sensitization as many times as needed to maintain a constant antibody titer, and blood samples may be collected in small quantities as needed for immediate use. It is also possible to obtain a monoclonal antibody in a usual manner by sensitizing a mouse with the enzyme and then forming hybridomas from spleen cells and myeloma cells of the sensitized mouse.

The present invention will hereinafter be described in further detail by the following examples and reference examples. It is however to be noted that the present invention are by no means limited by or to these examples.

REFERENTIAL EXAMPLE 1

Measurement of PAF Acetylhydrolase Activity (1) Using unlabeled lyso PAF (product of Bachem Feinchemikalien AG), 1-O-[1-$^{14}$C]hexadecyl-lyso PAF (product of New England Nuclear Company; hereinafter called the "labeled lyso PAF") was diluted to 4,000 dpm/nmol.

On the other hand, 1-O-hexadecyl-2-[$^{3}$H-acetyl]-sn-glycero-3-phosphocholine (hereinafter called "$^{3}$H-acetyl PAF") was diluted to 3,200 dpm/nmol with the unlabeled lyso PAF.

A standard culture system for the measurement of PAF acetylhydrolase was composed of 50 mM Tris-HCl (pH 7.4), 5 mM EDTA, 5 mM 2-mercaptoethanol (2-ME) and 20 nmol $^{3}$H-acetyl PAF. The total volume of the sample was 0.25 ml.

(2) Measurement of PAF acetylhydrolase activity was conducted by culturing a test sample in the above-described standard culture system at 37° C. for 30 minutes, adding 2.5 ml of chloroform/methanol (4:1 V/V) and 0.25 ml of water to terminate the reaction, and then measuring the radioactivity of a small amount (0.6 ml) of each upper layer to determine the amount of the acetate liberated from the $^{3}$H-acetyl PAF.

EXAMPLE 1

Obtainment of Bovine PAF Acetylhydrolase (1) A fresh bovine liver was purchased from a slaughterhouse and was then treated within 3 hours of the slaughter. Treatments were all conducted at 0 to 4° C. The liver was homogenized in a Waring blender subsequent to the addition of a homogenizing buffer [10 mM Tris-HCl (pH 7.4), 250 mM sucrose, 1 mM EDTA] in an amount 5 times as much as the liver. The resulting homogenate was centrifuged for 30 minutes under 100,000×g, followed by the removal of a solid portion. The resultant supernatant was centrifuged further for 1 hour under 100,000×g, whereby a dissolved portion was obtained (supernatant portion)

(2) The supernatant portion obtained through the procedures (1) was adjusted to 1 M with NaCl. Subsequent to stirring for 15 minutes, the solution was loaded on a "BUTYL TOYOPEARL 650 M" column which had been equilibrated beforehand with a buffer composed of 50 mM Tris-HCl (pH 7.4), 1 mM EDTA and 1 M NaCl. After the column was washed with the same buffer, proteins were eluted with a linear gradient of NaCl (1 to 0 M). PAF acetylhydrolase activity was eluted as a single peak in 1 to 0 M NaCl fractions.

(3) Active fractions from the "BUTYL TOYOPEARL" column were loaded on a "Q-Sepharosel" column which had been equilibrated with 10 mM Tris-HCl (pH 7.4), 1 mM EDTA and 20% (V/V) glycerol (buffer A). The column was washed with the buffer A. Proteins were eluted with a linear gradient of NaCl (0 to 500 mM) in the buffer A. The activity was observed in a fraction eluted with about 300 mM NaCl.

(4) The active fraction from the "Q-Sepharose" column was concentrated to about 6 ml in an "Amicon ultrafiltration cell" in which "YM-10" membranes were used. The thus-concentrated fraction was loaded on a "Biogel A-1.5 m" gel filtration column which had been equilibrated beforehand with 10 mM Tris-HCl (pH 7.4), 200 mM NaCl, 5 mM 2-ME, 20% (V/V) glycerol and 0.5% (W/V) "CHAPS" (buffer B). The activity was eluted as a single peak in a fraction corresponding to a molecular weight of about 40 kDa.

(5) The active fraction from the "Biogel-A 1.5 m" column was loaded on a hydroxyapatite column which had been equilibrated beforehand with 10 mM Tris-HCl (pH 7.4), 5 mM 2-ME, 20% (V/V) glycerol and 0.5% (W/V) "CHAPS" (buffer C). Proteins were eluted with a linear gradient which ranged from the buffer C alone to a buffer C containing 150 mM KH$_2$PO$_4$. The activity was observed in a fraction which was eluted with about 50 mM KH$_2$PO$_4$.

(6) The active fraction from the hydroxyapatite column was dialyzed against the buffer C, and was then loaded on an "FPLC Mono Q HR 5/5" column which had been equilibrated beforehand with the buffer C. Proteins were eluted by a linear gradient of NaCl (0 to 500 mM) in the buffer C. The activity was observed in a fraction which was eluted with 250 mM NaCl, and a protein in the fraction was obtained as purified bovine PAF acetylhydrolase.

The total proteins, total activities, purification degrees (in terms of times) and the like in the individual purification steps described above are tabulated below:

| Step | Total proteins (mg) | Total activity (μmol/min) | Activity per weight (nmon/min/mg) | Degree of purification (times) | Yield (%) |
|---|---|---|---|---|---|
| Cytoplasm | 46000 | 73.5 | 1.6 | 1 | 100 |
| BUTYL TOYOPEAL | 680 | 16.3 | 24 | 15 | 22 |
| Q Sepharose FF | 72.4 | 8.96 | 124 | 78 | 12 |
| Biogel A-1.5 m | 6.93 | 7.38 | 1060 | 670 | 10 |
| Hydroxyapatite | 3.45 | 5.29 | 1530 | 960 | 7.2 |
| Mono Q FPLC | 0.3 | 2.16 | 7200 | 4500 | 2.9 |

EXAMPLE 2

Determination of Amino Acid Sequence of Bovine PAF Acetylhydrolase (1) About 0.2 mg of the purified PAF acetylhydrolase obtained in Example 1 was reduced with 1 mg of dithiothreitol at room temperature for 2 hours, followed by the S-alkylation with 0.6% (W/V) 4-vinylpyridine at room temperature for 2 hours.

Using a 4.6 mm×250 mm "Vydak 304-1251 C$_4$" column which had been equilibrated beforehand with 20% (V/V) acetonitrile containing 0.1% (V/V) trifluoroacetic acid, the reaction mixture was subjected to reverse phase high-performance liquid chromatography (HPLC). Proteins were then eluted with a linear gradient of acetonitrile (20 to 85% V/V) which contained 0.1% (V/V) trifluoroacetic acid.

(2) 40 kDa polypeptide, which had been purified by the HPLC, was dialyzed against a lysylendopeptidase digestive buffer [0.5 M Tris-HCl (pH 8.5) and 4 M urea]. Next, 1 μg of a lysylendopeptidase was added to the sample. After the reaction mixture was incubated for 18 hours at 37° C., the reaction mixture was fractionated by reverse phase HPLC through a 4.6 mm×250 mm "Vydak 304-1251 C$_4$" column while using a linear gradient of acetonitrile (5 to 70% V/V) which contained 0.1% (V/V) trifluoroacetic acid.

(3) The amino acid sequence of a peptide fragment obtained by the reverse phase HPLC was determined by an automated sequencer ("Model 477A", trade name; manufactured by ApplIed Biosystems, Inc.).

The base sequence of the bovine PAF acetylhydrolase, which was determined from the amino acid sequence of the peptide fragment, was as shown above by the formula (III) (SEQ ID NO:4).

Further, from the peptide sequence (III) (SEQ ID NO:1)of the bovine PAF acetylhydrolase, a gene encoding the enzyme was determined by a method known per se in the art. The gene was found to be represented by the formula (IV) (SEQ ID NO:2).

EXAMPLE 3

Cloning of Non-active Human PAF Acetylhydrolase CDNA

Using as a template the bovine PAF acetylhydrolase cDNA obtained in Example 2, fluorescein-12-dUTP was incorporated in 500,000 clones of each of a fetal human liver cDNA library (pRc/CMV) and a human brain cDNA library (pCMV SPORTS) by PCR. The clones were then subjected to colony hybridization while detecting the labeling reagent by ECL, whereby cloning was conducted. As a result, a single positive clone was obtained from the human brain library.

A plasmid DNA was prepared and the base sequence was determined. The clone was a full-length clone which contained ATG encoding initiating methionine. Encoding 43 N-terminal amino acids were the same as the corresponding amino acids in the sequence of the bovine PAF acetylhydrolase up to the 40th amino acid, and there was poly A at the 3' end. A more accurate determination of the base sequence was conducted. As a result, the cDNA was found to consist of 2188 bp and to contain an ORF (open reading frame) consisting of 253 amino acids. Compared with the bovine PAF acetylhydrolase cDNA, 140 amino acids had been deleted. The segment of the deleted 140 amino acids contains a "catalytic triad" of serine, histidine and aspartic acid, which exhibits catalytic activity. The cDNA is therefore not believed to have PAD acetylhydrolase activity.

Hence, a primer was synthesized at positions flanking the deleted region, and PCR was conducted using the library DNA as a template. From the human brain cDNA, two bands were obtained, one corresponding to the above-described cDNA with the 140 amino acids deleted, and the other to a cDNA having substantially the same length as the bovine PAF acetylhydrolase cDNA. From the foregoing, the human brain library DNA was expected to contain, in addition to the above-obtained cDNA, a human PAF acetylhydrolase CDNA which is actually equipped with PAF acetylhydrolase activity.

EXAMPLE 4

Cloning of Human PAF Acetylhydrolase cDNA

The human brain cDNA library was diluted to give 2000 clones per well, followed by incubation on 5 96-well plates. Subpools consisting of 10 wells were prepared, and positive pools were determined by PCR (Pool Nos. 10, 20, 28, and 38). With respect to these subpools, PCR was conducted well after well, so that positive pools were confirmed (Pool Nos. 10-5, 20-10, and 38-12).

Concerning these pools, incubation was conducted on plates subsequent to dilution. Using the non-active human PAF acetylhydrolase cDNA as a probe, cloning was attempted by hybridization. Labeling of the DNA was conducted with fluorescein 12-dUTP by PCR, and detection was carried out by ECL. Positive colonies were obtained from Pool Nos. 10-5 and 20-10. Plasmid DNAs of these clones were replicated, and their base sequences were then determined. As a result, a human PAF acetylhydrolase cDNA represented by the formula (II) (SEQ ID NO:4) was obtained from the clones of Pool Nos. 10-5.

Based on the resultant cDNA, the amino acid sequence of the human PAF acetylhydrolase was determined. It was found to be represented by the formula (I) (SEQ ID NO:3). Up to 88%, the sequence was the same as that of the bovine PAF acetylhydrolase (346/392 amino acids). On the other hand, it was 42% identical to that of the plasma human PAF acetylhydrolase (162/392 amino acids).

Further, the above cDNA was incorporated in the pUC-Pl-cl vector, introduced in E. coli W3110 and then subjected to expression. A band, which corresponded to a protein having a molecular weight of 42 kDa, was detected by SDS-PAGE.

The protein was investigated for activity. Human PAF acetylhydrolase activity was confirmed.

What is claimed is:

1. An isolated recombinant protein comprising the amino acid sequence of SEQ ID NO:3.

2. The isolated protein of claim 1, which has platelet activating factor acetylhydrolase activity.

3. The isolated protein of claim 1, which is a human protein.

* * * * *